United States Patent [19]

Kiegel et al.

[11] 4,431,829
[45] Feb. 14, 1984

[54] PROCESS FOR THE PREPARATION OF 1,4:3,6-DIANHYDRO-D GLUCITOL 5-NITRATE

[75] Inventors: Einhart Kiegel, Mannheim; Karl Lauer, Schriesheim, both of Fed. Rep. of Germany

[73] Assignee: Boehringer Mannheim GmbH, Mannheim-Waldhof, Fed. Rep. of Germany

[21] Appl. No.: 276,773

[22] Filed: Jun. 24, 1981

[30] Foreign Application Priority Data

Jul. 30, 1980 [DE] Fed. Rep. of Germany ....... 3028873

[51] Int. Cl.$^3$ .......................................... C07D 307/00
[52] U.S. Cl. .................................................. 549/464
[58] Field of Search ......................... 260/467; 549/464

[56] References Cited

U.S. PATENT DOCUMENTS 3,886,186  5/1975  Dvonch et al. ..................... 549/464
4,065,488  12/1977  Chou et al. ..................... 260/467 X
4,297,286  10/1981  Sandrock et al. ................... 549/464

OTHER PUBLICATIONS

Carbohydrate Research 2 (1966), S. 122–131.

*Primary Examiner*—Leland A. Sebastian
*Attorney, Agent, or Firm*—Felfe & Lynch

[57] ABSTRACT

The present invention provides a process for the preparation of 1,4:3,6-dianhydro-D-glucitol-5-nitrate, in which
  (a) 1,4:3,6-dianhydro-D-glucitol is acetylated with 0.5 to 1.5 mole equivalents of acetic anhydride in the presence of a catalyst, a mixture of 1,4:3,6-dianhydro-D-glucitol-2-acetate, 1,4:3,6-dianhydro-D-glucitol-5-acetate and 1,4:3,6-dianhydro-D-glucitol-2,5-diacetate being obtained;
  (b) the mixture is nitrated with nitric acid, a mixture of 1,4:3,6-dianhydro-D-glucitol-2-acetate-5-nitrate and 1,4:3,6-dianhydro-D-glucitol-5-acetate-2-nitrate being obtained; and
  (c) hydrolysis is carried out with an inorganic base to give 1,4:3,6-dianhydro-D-glucitol-5-nitrate;
wherein, in step (a), the reaction is carried out in the presence of a basic catalyst and the 1,4:3,6-dianhydro-D-glucitol-2,5-diacetate is substantially removed before further working up.

5 Claims, No Drawings

PROCESS FOR THE PREPARATION OF 1,4:3,6-DIANHYDRO-D GLUCITOL 5-NITRATE

This invention relates to a new process for the preparation of 1,4:3,6-dianhydro-D-glucitol 5-nitrate (isosorbide 5-nitrate). More specifically, the present invention relates to a large scale and economical commercial process for such preparation. Isosorbide 5-nitrate is used for the treatment of coronary cardiac diseases, such as angina pectoris.

A series of processes for the preparation of this compound is known from the literature, which can be classified according to four basic principles.

(a) The direct nitration of isosorbide is described in Photochem., Photobiol., 4, 657/1965 and in Federal Republic of Germany Pat. No. 2,221,080. This process leads, in poor yield, to mixtures of isosorbide 2-nitrate and isosorbide 5-nitrate which must then be separated by an expensive and time-consuming process. Furthermore, in the case of this method, there is a danger that the explosive isosorbide-2,5-dinitrate is also formed simultaneously. (The term "nitration" used here and hereinafter is to be understood to mean the formation of a nitric acid ester).

(b) For this reason, the process described in Org. Magn. Resonance, 3,693/1971 and in Can. J. Chem., 45, 2192/1967, in which isosorbide-2,5-dinitrate is first prepared and then partly hydrolysed, is also unsuitable for use on a large scale.

(c) Federal Republic of Germany Pat. No. 2,903,927 describes a process for the preparation of the two isomeric isosorbide mononitrates which starts from isomannidol. This is, for example, first esterified with tosyl chloride to give isomannidol-2-tosylate which is then subjected to a Walden inversion, with, for example, potassium benzoate in an $S_N2$-reaction, to give isosorbide-2-benzoate. The unprotected hydroxyl group is then nitrated with nitric acid and the benzoyl radical is split off by partial saponification to give isosorbide-5-nitrate. A disadvantage of this process is the occurrence of various solvent and extraction mixtures, which are very laborious to regenerate, the introduction of a fourth stage, which reduces the yield, and the complicated purification operations, especially at the last stage. In particular, the solvent mixtures which occur and the laborious purification steps stand in the way of a large-scale use of this process.

(d) Some of the disadvantages involved in the process principle of (c) above disappear when starting from isosorbide instead of from isomannidol. Such a process is described in Federal Republic of Germany Pat. No. 2,751,934, as well as in the corresponding U.S. Pat. No. 4,065,488. Isosorbide is here first esterified with a lower alkanoic acid anhydride or lower alkanoic acid chloride or bromide, especially with acetic anhydride, to give a mixture of isosorbide, isosorbide-2-acylate, isosorbide-5-acylate and isosorbide-2,5-diacylate. In a second step, the isosorbide is extracted from the mixture in order, in the subsequent nitration step, to avoid the formation of the potentially explosive isosorbide-2,5-dinitrate. In a third step, the mixture of isosorbide-2-acylate, isosorbide-5-acylate and isosorbide-2,5-diacylate is then nitrated with nitric acid and the mixture obtained of isosorbide-2-acylate-5-nitrate, isosorbide-5-acylate-2-nitrate and isosorbide-2,5-diacylate is partially hydrolysed so that a mixture is obtained of isosorbide-2-nitrate, isosorbide-5-nitrate and isosorbide. Finally, the isosorbide-5-nitrate is isolated by crystallisation from appropriate solvents. The isosorbide-5-nitrate is apparently only formed in the process in a minor amount.

Therefore, it is an object of the present invention to provide a process with which isosorbide-5-nitrate can be prepared simply and economically on a large scale. It is thereby especially desired to avoid the occurrence of complex solvent mixtures which cannot be worked up since these would give rise to disposal problems and to environmental problems.

Thus, according to the present invention, there is provided a process for the preparation of 1,4:3,6-dianhydro-D-glucitol-5-nitrate wherein (a) 1,4:3,6-dianhydro-D-glucitol is acetylated with 0.5 to 1.5 mole equivalents of acetic anhydride in the presence of a basic catalyst, there being obtained a mixture of 1,4:3,6-dianhydro-D-glucitol-2-acetate and 1,4:3,6-dianhydro-D-glucitol-5-acetate in a ratio of greater than 1:1, as well as 1,4:3,6-dianhydro-D-glucitol-2,5-diacetate as by-product, from which mixture 1,4:3,6-dianhydro-D-glucitol-2,5-diacetate is removed, (b) the mixture thus obtained is nitrated with nitric acid, a mixture of 1,4:3,6-dianhydro-D-glucitol-2-acetate-5-nitrate and 1,4:3,6-dianhydro-D-glucitol-5-acetate-2-nitrate thereby being obtained, from which the 1,4:3,6-dianhydro-D-glucitol-2-acetate-5-nitrate is isolated, and (c) this latter compound is then hydrolysed with an inorganic base to give substantially pure 1,4:3,6-dianhydro-D-glucitol-5-nitrate.

It is especially surprising that, in step (a), under appropriate basic conditions, a ratio of 1,4:3,6-dianhydro-D-glucitol-2-acetate to 1,4:3,6-dianhydro-D-glucitol-5-acetate of greater than 1:1 is obtained.

According to a special embodiment of the process, in step (a) the 1,4:3,6-dianhydro-D-glucitol is reacted with 0.5 to 1.5 mole equivalents of acetic anhydride in an inert and in a basic solvent at a temperature of from 0° to 80° C. and, before step (b), the two solvents, the unreacted 1,4:3,6-dianhydro-D-glucitol, as well as the 1,4:3,6-dianhydro-D-glucitol-2,5-diacetate are removed.

Water-immiscible inert solvents are here to be understood those which do not participate in the course of the reaction. Examples of such solvents include methylene chloride, chloroform, benzene, toluene and cyclohexane, methylene chloride being especially preferred.

The basic solvent is, according to the present invention, to be understood to mean, for example, pyridine, triethylamine or picoline, pyridine being especially preferred.

According to an especially preferred embodiment of the process, in step (a), 1,4:3,6-dianhydro-D-glucitol is reacted with 0.5 to 1.5 mole equivalents of acetic anhydride in a mixture of methylene chloride and pyridine and, before step (b), the pyridine is removed by washing with sulphuric acid, the unreacted 1,4:3,6-dianhydro-D-glucitol by washing with water, the methylene chloride by distilling off and the 1,4:3,6-dianhydro-D-glucitol-2,5-diacetate, after precipitation, by filtration, the precipitation of the 1,4:3,6-dianhydro-D-glucitol-2,5-diacetate being brought about surprisingly simply by seeding, i.e. by adding a few crystals of the pure diacetate to the concentrated product mixture.

In the case of this method of operation, by means of simple operations which can be carried out on a large scale: both solvents, unreacted educt and resultant by-product are recovered; in the nitration step (b), the two monoacetates of interest are introduced with a diminished content of diacetate; and the occurrence of solvent mixtures which cannot be separated or can only be separated with difficulty is avoided.

The recovered 1,4:3,6-dianhydro-D-glucitol-2,5-diacetate can, in a further preferred embodiment of the process, be converted back into 1,4:3,6-dianhydro-D-glucitol by filtering through an ion exchanger in the H+ form and again used in the process, which is of considerable economic advantage.

It is to be regarded as being especially surprising that, in stage (b), after carrying out the nitration, it is possible to precipitate out the desired 1,4:3,6-dianhydro-D-glucitol-2-acetate-5-nitrate in high purity simply by diluting the nitrating acid with water and to separate it from the 1,4:3,6-dianhydro-D-glucitol-5-acetate-2-nitrate by-product by filtering off.

The positional isomeric 1,4:3,6-dianhydro-D-glucitol derivatives separated in this manner can now, by hydrolysis, be converted almost quantitatively into the desired 1,4:3,6-dianhydro-D-glucitol-5-nitrate or into 1,4:3,6-dianhydro-D-glucitol-2-nitrate, obtained as a by-product of the process.

The present invention also provides pharmaceutical compositions containing 1,4:3,6-dianhydro-D-glucitol-5-nitrate prepared by the process of the present invention, in admixture with a pharmaceutical diluent or carrier.

The following Example is given for the purpose of illustrating the present invention:

EXAMPLE

Step (a)

Acetylation of 1,4:3,6-dianhydro-D-glucitol

A mixture of 4.68 kg. isosorbide, 3.45 liters pyridine and 80 liters methylene chloride is stirred at ambient temperature until a solution is obtained. Thereafter, 3.80 liters acetic anhydride are added thereto, a noticeable warming up does not occur. The reaction mixture is left to stand for 48 hours at ambient temperature. A subsequent gas chromatographic investigation gives the following composition of the reaction mixture: 50.2% 1,4:3,6-dianhydro-D-glucitol-2-acetate, 6.3% 1,4:3,6-dianhydro-D-glucitol-5-acetate, 30.3% 1,4:3,6-dianhydro-D-glucitol-2,5-diacetate and 12.6% 1,4:3,6-dianhydro-D-glucitol. The methylene chloride phase is subsequently extracted with dilute sulphuric acid (1.16 liters concentrated sulphuric acid in 3.30 kg. ice). After separating off the sulphuric acid phase, the methylene chloride phase is further washed twice with 1.10 liter amounts of ice water. The wash water contains 1,4:3,6-dianhydro-D-glucitol and is, as described hereinafter, worked up together with the diacetate. The methylene chloride phase is now concentrated at 50° C. and 400 mm.Hg pressure to a syrup, the bath temperature being increased to 70° C. for 2 hours towards the end of the distillation with the application of a full water-pump vacuum in order to remove residues of acetic acid and pyridine. 5.5 kg. of a product mixture are obtained which, according to gas chromatographic analysis, contains 54.2% 1,4:3,6-dianhydro-D-glucitol-2-acetate, 6.2% 1,4:3,6-dianhydro-D-glucitol-5-acetate, 37.4% 1,4:3,6-dianhydro-D-glucitol-2,5-diacetate and 1.7% 1,4:3,6-dianhydro-D-glucitol. The proportion of 1,4:3,6-dianhydro-D-glucitol can be further reduced by further washing with water before stripping off the methylene chloride. The product mixture obtained is mixed with 3.5 liters ice water. After complete mixing, it is seeded with diacetate.

After standing overnight at 0° to 5° C., the greater part of the diacetate (1 kg.) crystallises out and is filtered off with suction and washed with 0.5 liter ice water, the wash water being combined with the original filtrate. The combined filtrates are concentrated in a vacuum to constant weight, 4.1 kg. of an anhydrous acetate mixture being obtained which, according to gas chromatographic determination, contains 67.2% 1,4:3,6-dianhydro-D-glucitol-2-acetate, 7.7% 1,4:3,6-dianhydro-D-glucitol-5-acetate, 21.6% 1,4:3,6-dianhydro-D-glucitol-2,5-diacetate and 1.3% 1,4:3,6-dianhydro-D-glucitol.

The separated diacetate is combined with the 1,4:3,6-dianhydro-D-glucitol-containing wash waters, made up to 5 liters with water and brought into solution at 90° C. This solution is passed at 90° C. through a cation exchanger column in the H+ form (the exchanger can be, for example, SP 112 of Bayer A.G.) with a residence time of 2 hours. The eluate is concentrated to give 1 kg. of a bright yellow syrup which consists of 1,4:3,6-dianhydro-D-glucitol and which crystallises completely upon standing.

The sulphuric acid pyridine extract obtained by the above process is mixed with 7.5 liters of dilute aqueous sodium hydroxide solution (2.5 liters of concentrated aqueous sodium hydroxide solution in 5 liters water) until a pH of 7 to 8 is reached. The pyridine separates out as the upper phase and is separated off, dried with 0.7 kg. of sodium hydroxide flakes and subsequently distilled.

Step (b)

1,4:3,6-Dianhydro-D-glucitol-2-acetate-5-nitrate

A mixture of 5.1 liters glacial acetic acid and 4.8 liters acetic anhydride is cooled to +2° C. in a cooling bath (−5° C.). 1.08 liters of highly concentrated nitric acid is added dropwise at a maximum internal temperature of +6° C. The nitration mixture is then stirred for 5 minutes at an internal temperature of +4° C. and then mixed, within the course of about 0.5 to 1 hour, with a solution of 3.85 kg. of acetate mixture from step (a) in 7.6 liters glacial acetic acid at an internal temperature of from 0° to 4° C. The reaction mixture is subsequently washed with 2.6 liters of glacial acetic acid, stirred for 1 hour in a cold bath (−2° C.) and then diluted with 145 liters water. The 1,4:3,6-dianhydro-D-glucitol-2-acetate-5-nitrate thereby crystallises out immediately. After stirring overnight at 0° C., the reaction mixture is filtered with suction to give 3.1 kg. of almost pure product. This product is then used directly in the next step without further purification.

Step (c)

1,4:3,6-Dianhydro-D-glucitol-5-nitrate 3.1 kg. 1,4:3,6-Dianhydro-D-glucitol-2-acetate-5-nitrate from step (b) are suspended in 24 liters water at ambient temperature. While maintaining a pH of from 10 to 12, 530 ml. of 40% aqueous sodium hydroxide solution are added thereto. The termination of the saponification can be recognised when the pH no longer drops, substantially everything is dissolved and starting material can no longer be detected by thin layer chromatography (elution agent methanol/methylene chloride 4:96 v/v; detection with a sulphuric acid solution of diphenylamine). The reaction solution is adjusted to pH 6.8 to 7 with 10 ml. concentrated sulphuric acid solution and then mixed with 8.7 kg. sodium chloride. 1,4:3,6-Dianhydro-D-glucitol-5-nitrate is thereby obtained in the form of a voluminous precipitate. It is extracted once with 12 liters of methylene chloride and twice with 8 liter amounts of methylene chloride. The combined methylene chloride extracts are dried with anhydrous sodium sulphate and evaporated, a glassy residue being obtained. This glassy residue is stirred at ambient temperature with 28 liters benzine (b.p. 40°–60° C.), the product thereby becoming crystalline and precipitating out in the form of a powder. The product is filtered off with suction and dried at ambient temperature. The yield is 1.815 kg.; m.p. 92/94—96° C.; $\alpha_{20}{}^D = +174.9$ (c=1% in methanol).

TLC: (methanol/methylene chloride 4/96 v/v; ligroin-diethyl ether-glacial acetic acid) uniform.

HPLC: 100%.

It is to be observed that the crystallised, dried 1,4:3,6-dianhydro-D-glucitol-5-nitrate is to be regarded as being an explosive material and is, therefore, to be handled with the appropriate precautionary measures. However, in practice, and this also applies to a production on a tonne scale, it is not necessary to isolate the product in the abovedescribed crystalline form.

On a large scale, it is preferable to proceed as follows: The glassy residue mentioned in step (c) is dissolved in acetone and the acetone solution is then sprayed on to lactose. After drying, there is obtained a so-called desensitised mass which consists of 1 part of 1,4:3,6-dianhydro-D-glucitol-5-nitrate and 4 parts of lactose. The product is used in this safe form for further working up, for example to give tablets. Of course, other appropriate adjuvants can also be used for the preparation of a desensitised mass.

It will be understood that the specification and examples are illustrative but not limitative of the present invention and that other embodiments within the spirit and scope of the invention will suggest themselves to those skilled in the art.

What is claimed is:

1. Process for the preparation of 1,4:3,6-dianhydro-D-glucitol-5-nitrate comprising (a) acetylating, at a temperature from 0° C. to 80° C., 1,4:3,6-dianhydro-D-glucitol with 0.5 to 1.5 mole equivalents of acetic anhydride in the presence of basic solvent acting as an acid acceptor and catalyst for the acetylation and an inert water immiscible solvent or solvent mixture, and substantially removing non-reacted 1,4:3,6-dianhydro-D-glucitol, and substantially all resulting 1,4:3,6-dianhydro-D-glucitol-2,5-diacetate from the reaction mixture;

(b) nitrating the product of step (a) including 1,4:3,6-dianhydro-D-glucitol-2-acetate with nitric acid to obtain a mixture comprising 1,4:3,6-dianhydro-D-glucitol-2-acetate-5-nitrate, isolating the 1,4:3,6-dianhydro-D-glucitol-2-acetate-5-nitrate, by precipitation through dilution of the nitrating acid with water and subsequent filtration; and (c) hydrolyzing the 1,4:3,6-dianhydro-D-glucitol-2-acetate-5-nitrate latter mixture with an inorganic base to yield 1,4:3,6-dianhydro-D-glucitol-5-nitrate.

2. Process as claimed in claim 1, wherein in step (a), 1,4:3,6-dianhydro-D-glucitol is reacted with 0.5 to 1.5 mole equivalents of acetic anhydride in a mixture of pyridine and methylene chloride and, before step (b), the pyridine is removed by washing with sulfuric acid, the unreacted 1,4:3,6-dianhydro-D-glucitol by washing with water, the methylene chloride by distilling off and the 1,4:3,6-dianhydro-D-glucitol-2,5-diacetate, after precipitation by filtration.

3. Process as claimed in claim 2, wherein the precipitation of the 1,4:3,6-dianhydro-D-glucitol-2,5-diacetate is achieved by seeding.

4. Process as claimed in claim 1, wherein the separated 1,4:3,6-dianhydro-D-glucitol-2,5-diacetate is converted back into 1,4:3,6-dianhydro-D-glucitol by filtration through an ion exchanger in the H+ form and again introduced into the process.

5. The process of claim 1, wherein the solvent used is selected from methylene chloride, chloroform, benzene, toluene, cyclohexane or a mixture thereof, and pyridine or triethylamine is used as acid acceptor and catalyst for the acetylation.

* * * * *

UNITED STATES PATENT AND TRADEMARK OFFICE

CERTIFICATE EXTENDING PATENT TERM
UNDER 35 U.S.C. § 156

PATENT NO.: 4,431,829

DATED: February 14, 1984

INVENTORS: Einhart Kiegel et al.

PATENT OWNER: Boehringer Mannheim GmbH

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

2 YEARS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks